United States Patent
Barbieri et al.

(10) Patent No.: US 11,302,445 B2
(45) Date of Patent: Apr. 12, 2022

(54) DRUG DOSING RECOMMENDATION

(71) Applicant: Fresenius Medical Care Deutschland GmbH, Bad Homburg (DE)

(72) Inventors: Carlo Barbieri, Crema (IT); Flavio Mari, Crema (IT)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 561 days.

(21) Appl. No.: 16/318,753

(22) PCT Filed: Jul. 14, 2017

(86) PCT No.: PCT/EP2017/067942
§ 371 (c)(1),
(2) Date: Jan. 18, 2019

(87) PCT Pub. No.: WO2018/015319
PCT Pub. Date: Jan. 25, 2018

(65) Prior Publication Data
US 2019/0244712 A1 Aug. 8, 2019

(30) Foreign Application Priority Data
Jul. 18, 2016 (EP) .................................. 16179993

(51) Int. Cl.
*G16H 50/30* (2018.01)
*G16H 50/50* (2018.01)
*G16H 20/10* (2018.01)

(52) U.S. Cl.
CPC ............. *G16H 50/30* (2018.01); *G16H 20/10* (2018.01); *G16H 50/50* (2018.01)

(58) Field of Classification Search
CPC ......... G16H 50/30; G16H 50/50; G16H 20/10

USPC .......................................................... 703/11
See application file for complete search history.

(56) References Cited

U.S. PATENT DOCUMENTS

| | | |
|---|---|---|
| 6,658,396 B1 | 12/2003 | Tang et al. |
| 2011/0045476 A1 | 2/2011 | Barken et al. |
| 2012/0220528 A1 | 8/2012 | Van Antwerp et al. |

FOREIGN PATENT DOCUMENTS

WO WO 2015/067956 5/2015

OTHER PUBLICATIONS

International Search Report and Written Opinion in Application No. PCT/EP2017/067942, dated Oct. 6, 2017, 9 pages.
Wikipedia [online] "Feedforward neural network," Retrieved on Jan. 11, 2017, Retrieved from the Internet: URL <https://en.wikipedia.Org/w/index.php7t itle= Feedforward neuralnetwork&oldid=7229 08670>, dated May 30, 2016, 2 pages.
International Preliminary Report on Patentability in Application No. PCT/EP2017/067942, dated Jan. 22, 2019, 6 pages.
Barbieri et al., "A new machine learning approach for predicting the response to anemia treatment in a large cohort of End Stage Renal Disease patients undergoing dialysis," Computers in biology and medicine 61:56-61, Jun. 2015.
Barbieri et al., "An international observational study suggests that artificial intelligence for clinical decision support optimizes anemia management in hemodialysis patients," Kidney international 92(2)422-429, Aug. 2016.
Barbieri et al., "Performance of a Predictive Model for Long-Term Hemoglobin Response to Darbepoetin and Iron Administration in a Large Cohort of Hemodialysis Patients," PLOS one 11(3):1-18, 2016.

*Primary Examiner* — Jerry Lin
(74) *Attorney, Agent, or Firm* — Fish & Richardson P.C.

(57) ABSTRACT

The present disclosure relates to a method for calculating or estimating at least one medical value based on several input values using artificial intelligence.

7 Claims, 1 Drawing Sheet

DRUG DOSING RECOMMENDATION

CROSS REFERENCE TO RELATED APPLICATIONS

The present application is the national stage entry of International Patent Application No. PCT/EP2017/067942, filed on Jul. 14, 2017, and claims priority to Application No. EP 1617993.7, filed on Jul. 18, 2106, the disclosures of which are expressly incorporated herein in entirety by reference thereto.

TECHNICAL FIELD

The disclosure relates to a method for calculating or estimating at least one medical value based on several input values and a device configured to perform such a method.

BACKGROUND

Drug dosage remains a challenging subject of medicine. Inter-individual differences in patients may require different drug dosages. Many variables influence results, including patient history, genetics, measurable biomarkers as well as the formulation of the relevant drugs.

Moreover, effects of dosage change can be slow. Often, a drug dosage needs to be adapted in order to keep a diagnostic value in a certain range. A dosage change may prompt a delayed change in the diagnostic marker such that an over-adaptation of the drug dosage is only spotted much later.

The slow feedback often results in diagnostic markers oscillating around the desired value with much of the time being spent outside the desired range of the marker, which may result in poor therapeutic outcome. In addition to this, oscillating marker levels necessitate frequent laboratory tests, which can be expensive and inconvenient.

Successful drug dosage, thus, requires such a large number of factors to be considered that finding the optimal drug dosage for an individual patient is almost impossible for a human being.

SUMMARY

In one aspect, this disclose describes a method for calculating or estimating a medical value based on several input values using artificial intelligence. This disclosure also describes a device configured to carry out the method. Additionally, a drug is described that can be delivered at a dose recommended by the method or the device. In one embodiment, the drug is erythropoietin.

Artificial intelligence is generally the ability of a device or a method to perform tasks by employing intelligence. Artificial intelligence may comprise or consist of knowledge-based systems, interference engines, expert systems, neural networks, data mining systems, machine learning systems and combinations thereof.

The digital storage means is defined by the feature combination described herein. Accordingly, the digital storage means, in particular a hard disc drive, CD or DVD, has electronically readable control signals, which are able to interact with a programmable computer system such that a method will be executed.

The computer program product is defined by the feature combination described herein. Accordingly, in another aspect, the computer program product has a program code stored on a machine-readable data medium for executing a method when executing the program product on a computer.

A computer program product can be understood as, for example, a volatile signal, a computer program which may be stored on a storage device, an embedded system as a comprehensive system with a computer program (e.g. an electronic device with a computer program), a network of computer-implemented computer programs (e.g. a client-server system, a cloud computing system, etc.), or a computer on which a computer product is loaded, executed, saved or developed.

The "term machine-readable data medium" as used herein denotes in certain embodiments a medium containing data or information, which is interpretable by software and/or hardware. The medium may be a data medium, like a disk, a CD, DVD, a USB stick, a flashcard, an SD card or the like.

A computer program can be understood as, for example, a physical, ready-for-distribution software product which comprises a computer program.

It also applies to the digital storage means, the computer program product and the computer program that all or some of the machine-executed steps of the method are prompted.

The computer program is defined by the feature combination as described herein. Accordingly, in another aspect, the computer program has a program code for the execution of a method when executing the program on a computer.

It is noted that whenever it is referred to mass or concentration or volume of a substance in the present specification, changes thereof are also contemplated, be it expressly mentioned or not.

Whenever numbers are mentioned herein, the skilled person understands these to be a lower limit. The person skilled in the art would thus read, e.g., "at least one" instead of "one", assuming this does not present a contradiction or inconsistency as recognised by the person skilled in the art. This interpretation is comprised by the present invention just as much as the interpretation that a number, such as "one", means precisely and exclusively that number, such as "exactly one", wherever this is physically possible as recognized by the person skilled in the art. Both interpretations are comprised by the present invention and both are valid for all numbers mentioned herein.

In the following, the use of the expression "may be" or "may have" and so on, may be understood synonymously with "in exemplary embodiments is" or "in exemplary embodiments has", respectively, and so on, and is intended to illustrate exemplary embodiments.

Whenever erythropoietin is mentioned herein, this comprises erythropoietin as well its derivatives as long as this does not lead to a contradiction as recognised by the person skilled in the art. Erythropoietin derivatives include Epoetin alfa, Epoetin beta, Darbepoetin alfa, Methoxy polyethylene glycol-epoetin beta (brand name: Mircera).

By employing the method in accordance with some embodiments described herein, doctors may achieve better results by applying the dosage recommendations. The patient can be either a human being or an animal. The patient may be healthy or sick. The patient may be in need of medical care or not.

Embodiments described herein may encompass some or all of the following features in arbitrary combination provided such a combination be not recognised by the person skilled in the art to be technically impossible.

In some embodiments, the at least one input value comprises a drug recommendation.

In some embodiments, the method may use stored experiences and/or rules on how to use experience as well as current input values to arrive at a dosage recommendation.

The input values, which may be used by the method, may be recently acquired measurements, for examples results of blood tests and/or urine tests. The input values may additionally include past test results such that the method takes into account a time course of one or several parameters.

In certain embodiments, the method uses input values reflecting the mass or the concentration of a substance in a blood and/or a urine sample.

The input values may comprise test results from blood, urine, tissue and/or saliva samples. The input values may further comprise patient sex, height, weight, body volume, body composition (e.g. by impedance measurement), body mass index, dialysis vintage, pre-dialysis systolic and/or diastolic blood pressure and/or age.

The input values may further describe the presence and/or severity of the following conditions: diabetes, vascular hypertension, chronic glomerulonephritis, polycystic kidney disease, ischaemic heart disease, heart failure, peripheral artery disease, stroke/cerebrovascular accident, chronic respiratory diseases and/or infectious diseases.

Input values may comprise one, several or all of the following: delta haemoglobin (e.g., from the previous month), ferritin, transferrin saturation index, iron dose(s), erythropoietin dose(s) (e.g., darbepoetin). The input values may comprise the latest value and/or the values for the previous 30, 60, 90 or more days.

In some embodiments, in dialysis patients, the input values for the method comprise one, several or all of the following: ultrafiltration volume, Kt/V, duration of dialysis treatments, date of treatment, predialysis and/or dry body weight, transmembrane pressure, transmembrane pressure time course, ultrafiltration rate and/or ultrafiltration rate time course.

The input values may include one or several of the following: electrolyte concentration ($Na^+$, $K^+$, $Ca^{2+}$, $Mg^{2+}$, $Cl^-$, $Fe^{2+}$, $Fe^{3+}$ etc.), glucose, urea, uric acid, creatinine, creatinine clearance, blood cell count (red blood cell count, white blood cell count, thrombocyte count etc.), erythrocyte properties (MCH, MCV, MCHC), total blood protein, triglycerides, cholesterol, HDL, LDL, ferritin, myoglobin, troponin, fructose, fructosamin, haematocrit (Hct), blood oxygenation, blood protein concentration (haemoglobin etc.), HbA1c, blood osmolality, hydration state, ammonia, lactate, blood alcohol, phosphate, liver function tests (e.g., albumin, AST, ALT, transaminases, alkaline phosphatase bilirubin (total and/or direct)), thyroid parameters (TSH, T3, T4 etc.), hormones, coagulation parameters (e.g., aPTT, PT, INR, fibrinogen, platelet function test values, thrombodynamics test values, coagulation factor levels, bleeding time), blood type, C-reactive protein, antibodies (e.g., autoantibodies (antiphospholipid etc.)), drug concentrations and/or infectious disease markers.

In some embodiments, the input values comprise genetic markers, e.g., derived from DNA sequencing, PCR or DNA microarrays. Markers may comprise disease susceptibility genes such as MHC class and/or II variants.

In certain embodiments, the input values may comprise an indicator of an anaemia state of the patient.

In some embodiments, the indicator of an anaemia state is the total mass or the concentration of haemoglobin (Hb) or changes thereof over time, etc.

In certain embodiments, the concentration or the mass is directly measured. In addition or alternatively, the input values may be derived indirectly from other values, which allow a sufficient approximation of the substance, such as haemoglobin (Hb) or the haemoglobin (Hb) state.

In some embodiments, the indicator of an anaemia state is the haematocrit (Hct), with the haematocrit (Hct) being understood to be a concentration.

In certain embodiments, the anaemia state of the patient is expressed by only one value such as Hb concentration or the Hct, etc.

The input values for dialysis patients may comprise the value at a single point in time or the value at several time points. This may be the case for one or several values. Possible input values may also include further patient data, such as disease state and severity and comorbidity with other conditions.

In one embodiment, the method provides recommendations for drug dosage in renal failure. Preferably, the method provides recommendations for an erythropoiesis stimulating drug, e.g., in patients with chronic renal failure. In an especially preferred embodiment, the method provides recommendations of erythropoietin (EPO) dosage, in particular in patients with anaemia related to chronic renal failure.

In one embodiment, the method provides a recommendation for an EPO dosage to be administered between two dialysis treatments or before, during or after a particular dialysis treatment of a patient.

In some embodiments, the method comprises an artificial neural network. In some embodiments, the method comprises a Bayesian network, a support vector machine or the like.

In one embodiment, the method is based on a neural network, which was trained using a large amount of historic medical data, preferably from dialysis patients. Preferably at least 100, more preferably at least 1000 datasets are used or were used to train the neural network.

In one embodiment, the neural network is trained using data from a certain cluster of patients. Patients from a cluster may have one or several defined or pre-defined or selected or pre-selected characteristics or attributes in common. One cluster of patients, e.g., may only comprise patients of over 65 years of age, other clusters may exclusively contain dialysis patients, patients with chronic renal failure, men only, women only, patients with a history of stroke and/or overweight patients according to body mass index, etc. Advantageously, providing a neural network trained on a relevant cluster of patients, recommendations of drug dosages may be improved over such neural networks, which were trained on an unselected set of patients.

In some embodiments, the neural network is trained by the user, using a training software running on the device or on a network of devices. In some embodiments, the device is already trained and ready to be used without further training. In some embodiments, the device is partially trained and may optionally or must be trained further before use. In some embodiments, the method comprises the training of the neural network. In other embodiments, the method excludes the training of a neural network, but employs a neural network, which has already been trained.

In some embodiments, parts or parameters of the method are chosen according to a certain environment. Such an environment could be a certain health care provider or certain health insurer or insurance plan, which prescribes the use of certain specific drugs. An environment could also be a certain region or country. Drug availability and availability of dosage forms may differ by region or country. Parts or parameters, which may be chosen according to the environment, may include weights of a neural network, design of a neural network and a reward function. In some embodiments, the datasets for training of the neural network may be chosen according to an environment, e.g., according to an environment similar or identical to the environment, in which the device is located.

In some embodiments, the environment may be manually set by the user. In some embodiments, the environment may be detected automatically by the device. E.g., the location may be detected by the device, e.g., by patient ID, product number of disposable material, IP address, cell tower position and/or satellite navigation.

In one embodiment, the method and/or the device are certified as a medical device. To this end, a risk assessment of the method may be carried out and may yield results in line with requirements of the relevant supervisory bodies, e.g., in the EU and/or the USA.

In some embodiments, the method provides a certain drug dosage to ascertain that a certain measurable diagnostic value remains inside a certain range or moves towards a certain range.

The measurable diagnostic value may be a value selected from the possible input values as described above. In certain embodiments, the measurable diagnostic value is a haemoglobin level. In this case, the method may provide a drug dosage to keep the haemoglobin level within a certain range, preferably between 10 and 12 g/dl of blood, more preferably between 10 and 11.5 g/dl of blood. The method may be carried out with other possible target haemoglobin ranges.

In some embodiments, the method is adaptive. That is, during application of the method, measurement values are fed into the method to further improve recommendations. For example, a drug dosage is recommended with the aim to yield a certain diagnostic value level. After a certain time, said diagnostic value is measured and provided to the method such that future recommendations may be improved.

In some embodiments, the neural network is designed to predict a diagnostic value depending on input values. For example, a neural network may predict a future diagnostic value (e.g. a laboratory value such as a haemoglobin level) depending on a past drug dosage and other patient related data.

In some embodiments, the method predicts the haemoglobin concentration at a certain time in the future based on the current haemoglobin level as well as further parameters, such as current drug dosages. For example, the method may predict haemoglobin levels in one, two or three months' time depending on current and previous haemoglobin levels as well as ESA prescription doses.

In some embodiments, data concerning several time points may be used as input for the neural network. After the network is trained, it can be used to make predictions on a measurable diagnostic value depending on input values, such as drug dosages.

In some embodiments, due to a differing frequency of parameter sampling (e.g., haemoglobin levels may be measured once per month while dialysis treatment-related parameters are collected three times per week), a merging logic combining the relevant parameters into a consistent temporal series of patient records may be created.

In some embodiments, the method may include a reward function, which provides a reward score depending on certain parameters, such as known or desired diagnostic values and/or drug dosages. The reward function may be employed to select a target diagnostic value, e.g., a desired diagnostic value associated with the desired outcome. The reward function may assign a reward score to each possible action, such as administering a certain drug dosage. Actions, which are positive for the patient, may receive a good, positive reward score while actions that worsen the state of the patient may receive a negative reward score. Preferably, actions, which contribute to the patient moving towards one or several targets, such as the targets mentioned herein, yield a positive reward score. At the same time, actions, which move the patient further away from one or several of the targets preferably yield a negative reward score.

In some embodiments, the method comprises the following steps:
 simulation of the effects of several drug doses
  selection of the dose that provided the optimal performance according to a reward function.

In some embodiments, the method provides as input values to the neural network: past measured values and simulated drug doses. In this way, the neural network may simulate future diagnostic values based on different simulated drug dosages. The simulated future diagnostic values may be stored in memory as part of the method together with the associated simulated drug dosages. Then, a simulated future diagnostic value may be selected according to a reward function (e.g., a future diagnostic value within a target range or closer to the target range than the current diagnostic value). The simulated drug dosage associated with the selected future diagnostic value may then optionally be recalled from memory. In this embodiment, the said simulated drug dosage may then considered to be the recommended drug dosage.

In some embodiments, only drug dosages are simulated, which are available in the relevant environment (e.g., location and/or provider).

In some embodiments, the method does not require simulation and/or memory storage, instead a reverse calculation obtains the wanted "input" simulated drug dosage from the given "future" diagnostic value.

In one embodiment, the diagnostic value is the haemoglobin level and one of the input values is an ESA drug dosage, preferably an erythropoietin dosage. The reward function in this case may provide a reward score dependent on two terms, one related to the current haemoglobin level and one related to the predicted haemoglobin level or a change in haemoglobin levels. For a given haemoglobin value, the optimal predicted haemoglobin level may be selected according to the reward function, e.g., by selecting the maximum reward score for the given haemoglobin value. The ESA dosage yielding said optimal predicted haemoglobin level may then be calculated using the neural network. The dosage of the ESA is preferably calculated according to doses, formulations and/or brands of ESA available in the relevant environment.

In some embodiments, the method may provide recommendations for several different drugs. In particular, if these drugs have identical active components, but different formulations, or have similar active compounds, a recommended dosage may have to differ. The tasks of recommending the dosages of those similar drugs may be similar enough to be able to be learnt efficiently by one neural network. In some embodiments, drug recommendations of unrelated drugs may be made using the same neural network.

In some embodiments, a neural network, pre-trained for one drug, may be re-trained for a different related or unrelated drug, such that a certain abstraction found regarding one drug is transferred to another drug.

The neural network optionally comprises one or more hidden layers. Preferably, the neural network comprises between 1 and 5, preferably 2 hidden layers. In one embodiment, the network comprises 2 layers with 10 neurons each.

In some embodiments, the neural network is used in deep learning and comprises a large number of hidden layers, preferably more than 5, 10 or 20 hidden layers.

In some embodiments, the method predicts a measurable diagnostic value, e.g., the haemoglobin concentration in the blood of a patient treated with a certain drug, e.g., an ESA. Preferably, the drug is erythropoietin and/or iron. Advantageously, in some embodiments, the method has a prediction mean absolute error (MAE) for the haemoglobin level in 1 months' time of less than 2 g/dl, less than 1 g/dl or less than 0.6 g/dl in a test dataset, which in some embodiments consists of data from patients with chronic renal failure. In some embodiments, advantageously, more than 90% of all prediction errors are lower than 2 g/dl or lower than 1 g/dl. Advantageously, such performance levels are usually sufficient in clinical practice.

In some embodiments, the recommended drug dosage is chosen by the method to ascertain that a certain measurable diagnostic value remains or moves towards a certain target range.

In some embodiments, advantageously, the method delivers dosage recommendations, which when followed lead to a haemoglobin concentration of between 10 and 12 g/dl. In some embodiments, the dosage recommendations lead to the prevention of abrupt changes in haemoglobin levels. In this sense, abrupt changes are such changes, which are higher than 1 g/dl haemoglobin per month. In a patient, who has a haemoglobin level of less than 9 g/dl, the preferable target for the next month may not lie in the regular target range, but instead is 1 g/dl away from the current value towards the target range. That is, a patient with a haemoglobin level of 8 g/dl has a target of 9 g/dl for the first month instead of 10 to 12 g/dl. In some embodiments, the reward function takes into account such target shifts.

In some embodiments, advantageously, the method delivers stable haemoglobin levels, wherein the changes in haemoglobin levels are less than 0.7, more preferably less than 0.5 g/dl per month.

In some embodiments, advantageously, the method achieves its targets with the least use of drugs possible. In some embodiments, advantageously, the total amount of erythropoietin is the lowest possible to achieve one or more of the targets described above.

In some embodiments, the method is carried out in the device.

In the following, when it is stated that the device "allows to" or "may" perform a certain function etc., this comprises the interpretation that the device is configured to perform such function.

In some embodiments of the device, the device comprises a self-contained treatment unit, surveillance unit and/or simulation unit. This may comprise treatment stations, sensors, networks and/or a simulation environment.

In some embodiments, the device comprises two or more parts which are not physically connected, but which are functionally connected or connectable. In some embodiments, some or all of these parts may be connected or connectable in the sense of an internet of things concept (IoT). In some embodiments, some or all of these parts are connected or connectable by a wired network and/or wireless network (e.g., Wifi or Bluetooth). Some or all of the said parts may be stationary or mobile. In particular, one or several sensors of the device may be physically separate, but functionally connected or connectable to at least one other part of the device, e.g., a display of the device and/or a computing unit of the device.

At least one of the two or more parts of the device may be at least partly independent from each other in power supply and/or may each have or be able to receive their own network address, e.g., their own IP address.

The device according to some embodiments may comprise and/or may be in signal communication with one or several sensors. In some embodiments, the sensors comprise haemoglobin sensors, preferably haemoglobin sensors as part of dialysis machines.

The device may be connectable or connected to a network in order to access patient data. For example, the device may be connected to a hospital information system to have access to data of the patient to be treated. A hospital information system in the sense of this application comprises such information systems comprising several hospitals. In this way, the device may have access to the data of several hospitals. In some cases, the device may also have access to data of different patients in order to train an artificial neural network as part of the method.

In some embodiments, the device provides the dosage recommendation via an output unit such as a display and/or a printer. A display may be a simple number display, an LCD (e.g., allowing detailed display of data) or the like. Alternatively or additionally, the device may provide the dosage recommendation remotely, e.g., via a wired or wireless network and/or via broadcast of electromagnetic waves and/or light. The device may incorporate a web server such that a user may interact with the device, e.g., via a web browser. The web server may allow providing input values to the device and/or receiving drug dosage recommendations.

In some embodiments, the device allows the transmission of data to the device and/or from the device to the user via speech. To this end, the device comprises a speech output unit and/or a speech recognition unit.

In some embodiments, the device has a data reader. In some embodiments, a data reader may read data from an information containing item that contains patient identification data. Such an item could be a patient ID card. The reader may in some embodiments read a patient ID number from the item. The item may in some cases be a card, preferably a smart card, a bracelet, a tag or a fob. The reader may use contactless or contact technology to read information from the item. The item may contain a magnetic strip containing information. The item may contain an integrated circuit, which contains information. The reader may read the card using, e.g., near field technology or by physically touching electric contacts on the card, which are connected to an integrated circuit on the card. In some embodiments, the item comprises a one-dimensional or a two-dimensional bar code, which contains patient information.

In some embodiments, the data reader can read biometric information. For example, some readers may be able to identify patients by their fingerprints.

The data reader may comprise a keyboard, a scanner, such as a barcode scanner, a camera, a magnetic strip card reader, an RFID tag reader, a near field communication reader and/or writer.

In some embodiments, the card to be read by the reader of the device contains a patient identification number. In other embodiments, the item—additionally or alternatively—contains information concerning laboratory results, vital data, current and/or previous prescription dosages and/or dates of past doctor visits. In some embodiments, the device may process the data stored on the card to recommend a certain drug dosage. Additionally or alternatively, the device may use the patient ID to recall data from an internal database or from a database to which the device is connected, preferably via a network.

In some embodiments, the device may contain a processor, a volatile and/or a non-volatile memory unit. The non-volatile memory unit may contain software, which implements at least one part of the method.

In some embodiments, the device may be updateable. Preferably, a non-volatile memory in the unit may be partially or entirely overwritable with new information. In this way, it may be possible to change the method to adapt to new circumstances or parameters. It may be desirable to update the device in order to account for additional drugs, dosage forms, formulations etc. In some embodiments, the device may be updated with a method comprising a different neural network. Such a neural network may be already trained using data from an additional number of patients.

In some embodiments, the device may also adapt the method to account for its own prediction accuracy. For example, the device may make a certain dosage recommendation to achieve a certain laboratory result, in particular a haemoglobin level. After a certain period, the device receives information as to the haemoglobin level actually achieved, e.g., by manual input, sensor reading and/or from a database via a computer network. The method may then be adapted to allow for better predictions. To this end, a neural network, which may be part of the method, may be trained repeatedly according to new results. The device may also receive updates by a remote software update mechanism, e.g., via the internet or private networks. The device may be designed such that an update may be propagated from a central server and/or peer-to-peer. Furthermore, the device may be updateable using the data reader mentioned above.

In some embodiments, the device may transmit patient data and prediction accuracy (e.g., the difference between a predicted diagnostic value and the diagnostic value actually measured) to a central information system such as a server. Such a central information system may use the data from one, several or many devices to improve the method, e.g., by training the neural network to include the additional patient and accuracy data. In that way, the method may improve continually. In some embodiments, the patient and accuracy data is exchanged without a central information system, e.g., in a peer-to-peer network of devices. Advantageously, a peer-to-peer network may function without a central server and may thus be more fail-safe and/or cheaper to implement than alternative solutions. The devices preferably possess the computing power to adapt and retrain the neural network, which may be part of the method, in a reasonable time, preferably over night or faster. Preferably, patient data is anonymised before transmittal.

In some embodiments, the device is integrated into, connectable or connected to an apparatus, which may provide health information. Such an apparatus may be used in diagnosis or therapy of a patient. Such an apparatus may comprise sensors to acquire patient data and/or may contain treatment parameters for the treatment of the patient. In some embodiments, the apparatus is a haemodialysis machine, a haemofiltration or a haemodiafiltration machine.

In some embodiments, the apparatus is or comprises a syringe pump (e.g., a perfusor). The device may prompt the apparatus, e.g., the syringe pump, to provide an amount of drug according to the drug dosage recommendation to a patient.

The apparatus may comprise at least one sensor to measure an input value, may then provide the input value to the device and may provide a drug to the patient according to a drug dosage recommendation of the device. E.g., a haemodialysis machine may measure a haemoglobin level in the blood and may then provide the measurement to the device, the device may then provide a dosage recommendation of an ESA and the haemodialysis machine may then provide the ESA at the recommended dosage to the patient, e.g., by adding the ESA to an extracorporeal blood circuit.

In some embodiments, the device described herein is a medical device, which is preferably based on prediction models. In some embodiments, the model comprises an anaemia prediction model. In particular, such a prediction model may be applied to patients undergoing chronic renal failure. Such patients may sometimes receive treatment based on erythropoietic stimulating agents and/or iron. In many cases, available guidelines do not lead to uniform success for all patients.

In order to qualify as a medical device, the relevant national and international bodies frequently require a risk assessment. Furthermore, in order to estimate the risk, it is usually required to precisely define the intended use of the device. In some embodiments, the device is intended to be used in the treatment of anaemia, preferably in patients with anaemia associated with chronic renal failure.

In one embodiment, the device has all the features and properties required to comply with and/or is certified according to all the rules and directives required for a medical device in a particular region or state. In particular, preferred devices qualify as medical devices in the EU, USA, Switzerland, UK, Russia, China, South Africa and/or Brazil. Preferred devices comply with the Medical Device Directive (MDD) according to the relevant European Regulations of the European Union.

In one embodiment, the recommended dosage is communicated by the method to the physician in the same way as the haemoglobin level itself. That is, the dosage recommendation may be printed on the same sheet of paper, which contains the laboratory results. Advantageously, this may allow implementation without any additional output units as already available output units (such as displays, printers, etc.) are used.

In one embodiment, the dosage recommendation is displayed online or in a hospital information system together with the laboratory results for haemoglobin levels. In this case, the method may be carried out by the laboratory, which measures the haemoglobin values.

Advantageously, the laboratory stores the past haemoglobin levels of the patient. The past drug dosages and other parameters required by the method may be transmitted to the laboratory automatically, individually and/or are already contained in the laboratory database of past measurements of required parameters. In one embodiment, the method may be carried out by the haemoglobin analysis device. In other embodiments, the method may be carried out by laboratory software, a hospital information system or a software employed in a doctor's surgery.

In some cases, an embodiment is a self-contained treatment environment, supervision environment, and/or simulation environment. This environment comprises treatment stations, sensors and a network.

In addition to blood laboratory results, sensors may be integrated into treatment stations. In the case of erythropoietin as drug to be administered, sensors in haemodialysis devices may be used, e.g., haemoglobin sensors.

Some or all of the above embodiments of the device and/or the method as described herein can provide one, several or all of the following advantages:

The method and/or the device may more successfully consider all the relevant factors and process larger amounts of data than is feasible for a human being. Thus, the method may yield better drug dosage recommendations. Better may here be understood to mean that, when such better recommendations are followed, the target diagnostic value influenced by the drug dosage is in its target range for a larger proportion of the time than when a physician prescribes the dosages according to guidelines.

The better drug dosage recommendations may mean that the number of blood tests per unit time may be reduced without negative impact on the patient's health as predicted diagnostic values match real diagnostic values. In other words, as the result of the blood test may be predicted with high accuracy, the blood test may not need to be carried out as frequently. A lower number of blood tests may mean a reduction of data in hospital and/or laboratory information systems leading to a reduced requirement of memory storage and computing power.

An amplitude of oscillation of the diagnostic value influenced by the drug dosage may be reduced as a more precise drug dosage is achieved. This may mean that a larger proportion of the measured diagnostic value is inside the target range. It may further mean that drug use may be reduced, e.g., because large drug doses are saved when the diagnostic value goes below the lower boundary of the target range. Drug use may further be reduced, because the drug dosage may be precise enough for the method and/or device to target a sub-range at the lower end of the target range.

The method or device may produce more reliable dosage recommendations as well as a drug concentration.

All or some of the advantages mentioned above may also be found when applied to other substances than Hb and erythropoietin, which were only used herein by way of example.

Equally, all or some of the advantages of the method as mentioned above may apply to the device and vice versa.

Other aspects, features, and advantages will be apparent from the description, FIGURE, and claims. In the following, purely exemplary embodiments are described.

DETAILED DESCRIPTION OF THE FIGURES

Figure 1:
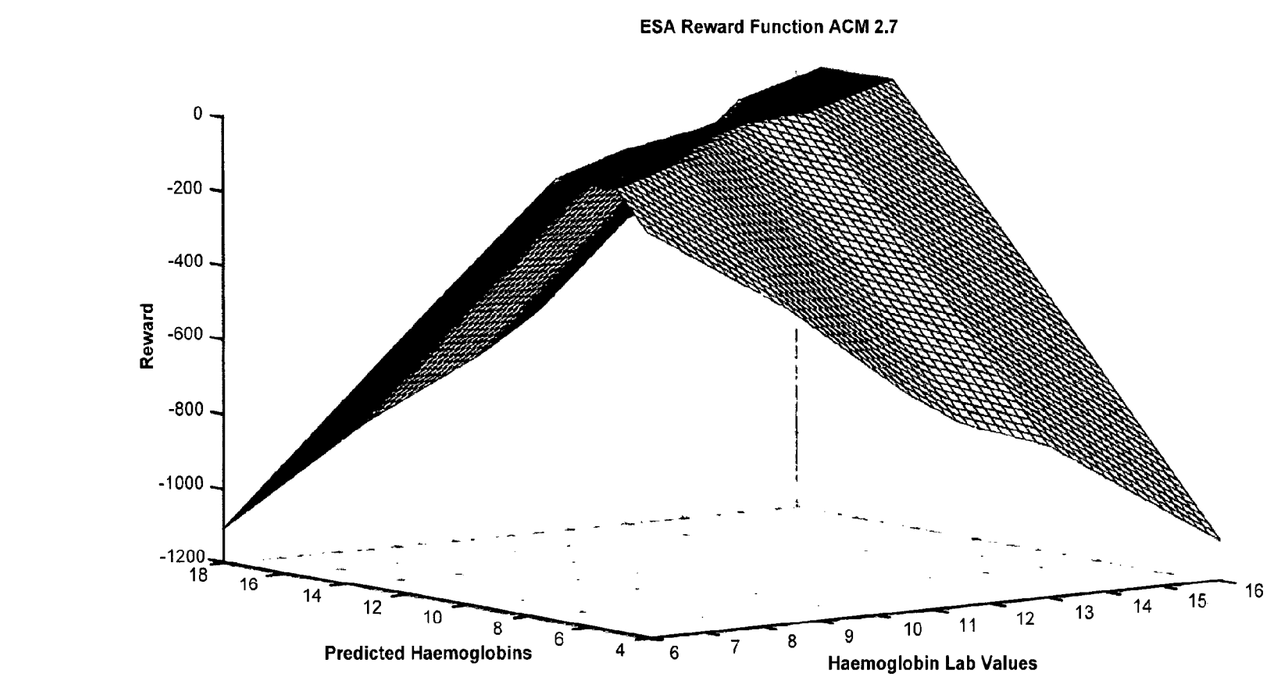
FIG. 1 shows the 3-dimensional graph of a reward function

FIG. 1 shows a graphical representation of a preferred embodiment of a reward function, which may be more easily understood than the mathematical function that produced it. The reward function is a mathematical function or an algorithm, which returns reward score when given the current haemoglobin and the predicted haemoglobin values. The reward function may differ for different drugs and drug dosage forms. The available drugs and drug dosage forms may depend on the country such that the relevant reward function may differ from country to country.

The usual approach for anaemia management in dialysis clinics is based on an assessment of the haemoglobin levels (normally performed on a monthly basis). Depending on haemoglobin levels, other laboratory results and received drug dosages as well as patient characteristics and physician review, drug dosages of ESA and iron are adapted. The method is preferably designed to suggest a new dosage of ESA and/or iron every time a haemoglobin level is measured.

In one embodiment, the method is at least partially developed using Matlab Artificial Neural Network Toolbox compiled into a Microsoft .Net library, which is then embedded in a web service developed within the Microsoft .Net Framework. The resulting application has—by way of example—no user interface as its communication with third-party systems is performed through a web service. No patient data is persisted since all the information needed to provide the prediction is provided by third-party systems. Calls to the method are synchronous and are performed by the third-party system. The suggested dose is in this embodiment obtained in a two-step procedure: First, a simulation of the effect of different ESA doses. Second, a selection of that dose which provided the optimal performance according to the criteria defined in the reward function, e.g., that dose which is associated with the maximum reward score.

For an embodiment of the device as a medical device, many considerations arise. There are many legal and technical aspects to take into account in order to fulfil the Medical Device Directive (MDD) under European regulation. In an embodiment, the method and/or the device qualify as medical device according to the MDD. In this embodiment, the method and/or device have a well-defined intended use and a detailed risk analysis.

In one embodiment the method and/or device has the intended use of supporting doctors in managing anaemia drug therapy. In particular, some embodiments analyse patient data sent by a third party system (clinical system) and performs a suggestion for the best ESA and/or iron dosage and scheduling to move the haemoglobin level towards a certain target range and for maintaining the haemoglobin level within said target range. Doctors are required to review the suggestions in a case-by-case procedure.

The method preferably comprises two sub-methods: a predictor model and an algorithm that makes use of the predictor algorithm to suggest the optimal therapy.

In one embodiment, both sub-systems may be implemented as computer programs. They are not necessarily part of a physical device, in which case not all the advantages stated above may be provided. In this case, no physical material is used to implement the method.

In some embodiments, the predictor model is implemented as a multilayer perceptron (MLP) feed-forwards artificial neural network (ANN). In other embodiments, the predictor model is implemented as a Bayesian network, a support vector machine or the like.

In some embodiments, a policy extractor is implemented by means of an algorithm that comprises or consists of a set of environment states S, a set of actions A, a set of rules to reward actions (e.g., by providing a reward score), a set of rules to control anomalous situations and/or selection criteria for the optimal action.

In some embodiments, the state S(t) represents a patient clinical status at time t while the action A(t) represents the suggested ESA. The set of actions may have some constraints in order to make the device more useful, e.g., only dosages and drugs available on the local market may be prescribed and the dosages must be kept within limits set by local guidelines. To this end, the method may be adapted by location.

In some embodiments, the policy extractor works using information provided by experts in terms of clinical targets (or simply implementing guidelines). It may simulate different dosages in order to select the optimal one.

In some embodiments, specific upper limits of ESA dosages as well as haemoglobin upper limits for ESA therapy interruption may be imposed by the method as specified by the relevant anaemia therapy guidelines such that potentially dangerous doses may be avoided (e.g., the method may ensure that ESA therapy must be interrupted when haemoglobin concentration is higher than 13 g/dl of blood).

In one embodiment, the population used to develop the method is formed by End-Stage Renal Disease (ESRD) patients, who follow stable haemodialysis (HD) and are affected by secondary anaemia (defined as low levels of plasma haemoglobin) and receive a pharmacological treatment for anaemia correction (i.e., ESA therapy). In this embodiment, pre-dialysis, peritoneal dialysis, internal care patients and patients under the age of 18 may not be included in the population used.

In some embodiments, the prescriptions suggested by the method may not become actual prescriptions without external medical intervention. In this case, the method is merely an aid to the doctor, the output of which the doctor may follow or ignore. The use of the method then involves continuous clinical supervision and control action such that clinical specialists only prescribe the relevant drug after receiving the output of the method as well as the patient's clinical condition.

In some embodiments, the method is trained on real patient retrospective data, i.e., actual clinical and/or biochemical data together with drug quantities actually administered. The method then reflects true therapeutic policies and produces its output based on real experience.

In some embodiments, if the method is trained on prescriptions by real doctors, it is thereby trained to respect the limits and thresholds used in real medicine.

In some embodiments, the method does not formulate drug prescriptions autonomously, but only provides suggestions to doctors.

In some embodiments, the device does not administer any kind of substance directly. In other embodiments, the device may deliver a drug to a patient in the dosage as provided by the method.

In some embodiments, erroneous, inconsistent or unusual data and/or data indicating danger to the patient may be detected. In these cases, the method may indicate these to the user, e.g., by providing an alert.

In some embodiments, no suggestion is produced if the input data is incomplete and/or inconsistent.

In some embodiments, the method is implemented on a central server and may be accessed remotely by clinicians. As such, the method and/or device do not compromise or endanger the clinical condition or safety of patients or users due to ergonomic features of the device, the package, transport or storage, the direct contact with production materials (both synthetic or natural, including materials of animal origin), the risk of toxicity, flammability, explosion, material deterioration, infections, any kind of contamination or incompatibility with biological tissues, the risk of electric accidents, mechanical or thermal risks, the production of contaminants or residues, the incorporation, the administration or the leaking of any kind of substance in/from the device (medicaments or any other, including blood derivatives), the respect of sterile conditions, the emission of radiation and/or the use in conjunction with other medical devices.

In order to acquire a MDD certification, a risk assessment is required. This requires the identification, classification and reduction of potential risks caused by the use of the medical device. Those risks are identified according to the intended use of the device.

The risk may be computed as the product of probability (table 1) and severity (table 2), as shown in table 3. According to certain corporate procedures, risk may be evaluated as "broadly acceptable" when its risk level is less than 10 and the probability is less than 6 (i.e., the risk category of a frequent hazard is not "broadly acceptable"). A risk may be "as low as reasonably practicable (ALARP)" if the computed risk level falls into one of these three categories: 10<=risk<15 or risk=6 when deriving from severity level 1 and probability level 6 or risk=15 when deriving from severity level 3 and probability level 5. A risk may be "not acceptable" if the computed risk falls into one of these two categories: risk>=16 or risk=15 when deriving from severity level 5 and probability level 3. According to ISO 14971 (2012) and certain corporate procedures, the "acceptable" class includes both the "broadly acceptable" risk category (i.e., risk<10 with probability level<6) and ALARP risk category (i.e., 10<=risk<15, risk=6 when deriving from probability level 6, risk=15 when deriving from probability level 5). Nonetheless, for all ALARP and "not acceptable" risks, a mitigation may be proposed to reduce each risk to the "broadly acceptable" or at least ALARP risk category.

In a test case, based on the hazard, six classes of risk (Table 1) and five severity categories (Table 2) were defined according to corporate procedures on risk management.

TABLE 1

Risk classes and their probabilities

| N | Class | Probabilities |
|---|---|---|
| 6 | Frequent | $p >= 10^{-2}$ |
| 5 | Probable | $10^{-3} <= p < 10^{-2}$ |
| 4 | Occasional | $10^{-5} <= p < 10^{-3}$ |
| 3 | Remote | $10^{-7} <= p < 10^{-5}$ |
| 2 | Improbable | $10^{-9} <= p < 10^{-7}$ |
| 1 | Incredible | $P < 10^{-9}$ |

TABLE 2

Severity Categories: Definition and Description

| N | Class | Definition | Description |
|---|---|---|---|
| 1 | Negligible | Malfunction without a significant consequence | Reversible (in one month) and non-life-threatening harm with no symptoms |
| 2 | Marginal | Evident temporary disturbance of the well-being of one patient, user or third party per occurrence | Reversible and non-life-threatening harm with mild symptoms |

TABLE 2-continued

Severity Categories: Definition and Description

| N | Class | Definition | Description |
|---|---|---|---|
| 3 | Critical | No death, but serious temporary deterioration in state of the health of one patient, user or third party per occurrence | Live threatening harm |
| 4 | Serious | Death or serious deterioration in the state of health with permanent impairment of one patient, user or third party per occurrence | Severe impairment of patient conditions or death of one patient |
| 5 | Catastrophic | Death or serious deterioration in the state of health with permanent impairment of more than one patient, user or third parties per occurrence | Severe impairment of several patients' condition or death of more than one patient |

TABLE 3

Risk Evaluation Sheet

| | | | | | |
|---|---|---|---|---|---|
| Frequent | 6 | 12 | 18 | 24 | 30 |
| Probable | 5 | 10 | 15 | 20 | 25 |
| Occasional | 4 | 8 | 12 | 16 | 20 |
| Remote | 3 | 6 | 9 | 12 | 15 |
| Improbable | 2 | 4 | 6 | 8 | 10 |
| Incredible | 1 | 2 | 3 | 4 | 5 |
| | Negligible | Marginal | Critical | Serious | Catastrophic |

Considering the intended use of the method in some embodiments, in which the method is implemented purely in software, risks in the use of the method may derive exclusively from erroneous dosage elaboration. Incorrect outcomes of the method cause from uncritical (asymptomatic and entirely reversible) to catastrophic events (including patient death).

In addition to the device intrinsic random error, unreliable and hazardous outcomes may depend on specific limits of the method in some embodiments, such as the inability of managing emergency or acute events. Although, in some embodiments, the method may contemplate all the standard information used by physicians to select the ESA and/or iron prescription, if patients are in some special condition, additional information may be needed to evaluate the optimal therapy. The learning process of the method may be less efficient for unusual occurrences and this may diminish the system prediction efficiency during unusual situations. In some embodiments, the method may include a rules-based system to identify unusual situations to adapt the output of the method and/or alert the user to the situation. Prediction and handling of special situations, in some embodiments, may not be the intended use of the method. In addition to recommendations by the method, physicians' intervention may also be required to identify those symptoms, which cannot be corrected by mere ESA and/or iron therapy (e.g., correction of hydration status, management of infections, bleeding etc.).

Risks in the use of the method may also derive, indirectly, from the use of incorrect input data. This may be a fake risk since it does not depend on the functioning of the method, but on previous mistakes, which may also influence physicians' errors, because they may access the same data, which the method uses to make dose suggestions.

In some embodiments, the method and/or the device may be certified according to the MDD of the European Union.

In some embodiments, the dose selection process may be deterministic, thus when the prediction of the next haemoglobin level is correct, the automatically selected dose is correct.

For this reason, the risk of an erroneous dosage suggestion may be related to a poor performance of the predictive model. Therefore, in some embodiments, it may be of paramount importance to evaluate the probability of an erroneous prediction and its consequences in those situations, which could generate a risk for the patient. An important machine learning paradigm may be the separation between training data and data used to test the performance of the model. Models are generally not only tested on their capability to describe the data used to train them, but also on the capability to generalise and perform correct predictions on unseen examples.

In one embodiment, the method comprises a database of different guidelines and/or different availability data (concerning available drugs and their dosages) for different locations.

In one embodiment, the method consults an external database periodically to check the available drugs and/or their dosages and/or the recommendations of the current guidelines.

In other embodiments, the method updates a database provided externally, e.g. via a network or a data reader. Alternatively or additionally, the user may enter locally available drugs, their dosages and/or guideline recommendations. In some embodiments, the method recognises its location and chooses the correct database.

In some embodiments, the location may be chosen manually by the user. In some embodiments, the device is issued with a permanent database, which cannot be changed by the user in order to prevent undesired modifications.

When a suggestion is generated by the method, there may be two main undesirable situations that may arise: first, doses with an undesired and unexpected outcome; and second, those in which the undesired outcome can be expected.

The first case may be caused by a number of reasons (e.g., intermittent events or a very unusual clinical condition) and it cannot be considered a malfunction of the method since the doctor might have likely committed the same mistake; therefore, the method might not generate an additional risk. However, for the sake of safety, any error committed by the method may be considered a potential risk for the patient in the proposed approach.

The second case is different since the doctor's knowledge and experience may lead to the realisation that the prediction of the method is not optimal. It is crucial to mitigate the risks that may appear in the use of the medical device. In this case, mitigation may be linked to the fact that the method may just produce suggestions. Thus, the doctor can evaluate and—where applicable—reject suggested doses that may not be optimal for the patient.

high to produce a decrease in the haemoglobin level, which will probably remain above target. Furthermore, the excessive dose suggestion might eventually cause access thrombosis.

For one example embodiment, table 4 shows all possible events that might cause hazards for the patient's health due to an erroneous method prediction for next-month Hb concentration, according to the two main sources of risk mentioned above; estimated probabilities are also shown.

TABLE 4

Risks and associated probabilities linked to overestimated predictions (>1.5 g/dl) and underestimated predictions (<1.5 g/dl) in one embodiment

| Risk Code | Hb (g/dl) | predictedHb-nextHb | Probability | Probability level | Hazard | Severity level | Risk level |
|---|---|---|---|---|---|---|---|
| R01 | <7 | >1.5 (overestimate) | $1 \times 10^{-5}$ | 44 | Very critical anaemic status not solved | 4 | 16 |
| R02 | [7, 8[ | >1.5 (overestimate) | $1 \times 10^{-4}$ | 4 | Almost critical anaemic status not salved | 3 | 12 |
|  |  |  |  |  | Almost critical anaemic status exacerbated | 4 | 16 |
| R04 | [8, 9[ | >1.5 (overestimate) | $6 \times 10^{-4}$ | 4 | Anaemic- status not solved | 2 | 8 |
|  |  |  |  |  | Anaemic status exacerbated | 3 | 12 |
| R06 | [9, 10[ | >1.5 (overestimate) | $2 \times 10^{-3}$ | 5 | Mild anaemic status not solved | 1 | 5 |
|  |  |  |  |  | Mild anaemic status exacerbated | 2 | 10 |
| R08 | [10, 11] | >1.5 (overestimate) when nextHb decreases | $4 \times 10^{-3}$ | 5 | Patient goes into a mild anaemic status | 1 | 5 |
| R10 | ]11, 12] | <-1.5 (underestimate) when nextHb increases | $6 \times 10^{-3}$ | 5 | Patient haemoglobin goes above targets | 1 | 5 |
| R13 | ]12, 13] | <-1.5 (underestimate) when nextHb increases | $3 \times 10^{-3}$ | 5 | Patient haemoglobin remains slightly above target (i.e., goes from 12 to 13) | 1 | 5 |
|  |  |  |  |  | Patient haemoglobin increases clearly above targets (i.e. goes from 12.5 to 14) | 2 | 10 |
| R14 | ]12, 13] | <-1.5 (underestimate) when nextHb increases. Patient is dialyzed with arteriovenous fistula | $2 \times 10^{-3}$ | 5 | Patient haemoglobin remains slightly above target (i.e., goes from 12 to 13) | 2 | 10 |
|  |  |  |  |  | Patient haemoglobin increases clearly above target (i.e., goes from 12.5 to 14) | 3 | 15 |

In one embodiment, mitigations may be proposed for all ALARP and "not acceptable risks", that is, risk >=10 and for negligible-frequent risks.

The actual risk of a wrong dosage suggestion may be related to the possibility of an erroneous prediction of the method. Therefore, in one embodiment, the proposed approach is focussed on evaluating the probability of an erroneous prediction and its consequences in all those situations that might generate a risk for the patient. In certain cases, two main possible sources of risk for the patient have been identified. The first potential risk may occur when the haemoglobin level is low and the method overestimates the next haemoglobin level more than 1.5 g/dl, that is, predictedHb>nextHb+1.5. The second potential risk may appear when the haemoglobin level is high and the method underestimates the next haemoglobin level more than 1.5 g/dl, that is, predictedHb<nextHb-1.5. In the former case, the resulting ESA suggestion might be too low to produce an increase in the haemoglobin level, and as result, the patient might remain mildly or strongly anaemic for another month. In the latter case, the resulting ESA suggestion might be too The probability of a hazard may be recalculated whenever the method changes, e.g., each time the neural network is retrained.

In one embodiment, the method was tested in a network of clinics over a period of 6 months. The a-posteriori probabilities for all risks mentioned in Table 4 were computed in those cases, in which the method suggestions were confirmed, i.e., the administered monthly dose coincided with the suggested monthly dose. That involved a total of 11508 suggestions, corresponding with 3,876 patients. Table. 5 summarises the difference between, a-priori and a-posteriori probabilities. A-posteriori probabilities turned out to be very similar to those estimated a-priori, with the only exception of Risk 8, where the a-posteriori probability almost doubles that stated in the Risk Management File; nonetheless, despite this case being the worst scenario, both probabilities are still of the same order ($\sim 10^{-3}$), thus reinforcing the confidence in the assessment of probabilities concerning the method.

TABLE 5

Comparison of a-priori and a-posteriori probabilities for the different risk codes shown in Table 4

| Risk Code | Probability stated in Risk Management File | A-posteriori probability |
|---|---|---|
| 1 | $1 \times 10^{-5}$ | 0 |
| 2 | $1 \times 10^{-4}$ | $8.6898 \times 10^{-5}$ |
| 4 | $6 \times 10^{-4}$ | $7.8206 \times 10^{-4}$ |
| 6 | $2 \times 10^{-3}$ | $2.52 \times 10^{-3}$ |
| 8 | $4 \times 10^{-3}$ | $7.3862 \times 10^{-3}$ |
| 10 | $6 \times 10^{-3}$ | $5.5613 \times 10^{-3}$ |
| 13 | $3 \times 10^{-3}$ | $3.8234 \times 10^{-3}$ |
| 14 | $2 \times 10^{-3}$ | $2.4331 \times 10^{-3}$ |

In certain embodiments, the method and/or the device are not targeted at and/or are not suitable for use and/or are not configured to be applied to inflammatory diseases, in particular in inflammatory bowel diseases (IBD), in particular in the diagnosis or prognosis of such diseases.

In certain embodiments, the method does not calculate, not predict and/or not estimate medical values (such as drug dosages), which are relevant in inflammatory diseases, in particular in IBD.

In certain embodiments, the method does not take as input values dosages of drugs, which are relevant in inflammatory diseases (in particular in IBD), or markers, which are characteristic and/or relevant in inflammatory diseases, in particular in IBD. Inflammatory bowel diseases include Crohn's diseases and ulcerative colitis.

In some embodiments, no ESA level, in particular no erythropoietin level, is used as an input value to the method.

In some embodiments, the method does not include a dose-response relationship, a dose response assessment and/or a dose-response database.

In certain embodiments, the method does not calculate, not predict and/or not estimate drug dosages for natriuretic peptide or derivatives thereof.

In some embodiments, the method does not include the delivery of a drug, in particular of natriuretic peptide or derivatives thereof.

For the avoidance of doubt, the present application may be directed to the subject matter described in the following paragraphs:

1. A method for calculating or estimating a medical value based on several input values using artificial intelligence.
2. The method according to paragraph 1, wherein the medical value is a recommended drug dosage.
3. The method according to paragraph 2, wherein the recommended drug dosage is recommended by the method to ascertain that a certain measurable diagnostic value remains or moves towards a certain target range.
4. The method according to one of the previous paragraphs, wherein the method is targeted at anaemia control.
5. The method according to paragraph 4, wherein the diagnostic value is a haemoglobin level.
6. The method according to paragraph 5, wherein the target range of haemoglobin is between 10 and 12 g/dl.
7. The method according to paragraph 3 to 6, wherein the input values comprise at least one past measurement of the diagnostic value and/or at least one past dosage of the drug, which dose is to be recommended.
8. The method according to one of the previous paragraphs comprising a merging logic for combining input values into a consistent temporal series.
9. The method according to paragraph 2 to 8, wherein the method provides recommendations for several different related and/or unrelated drugs.
10. A device configured to carry out the method according to one of the preceding paragraphs.
11. The device of paragraph 10, wherein the device is certified as a medical device.
12. The device of paragraph 11, wherein the device is certified as a medical device according to the Medical Device Directive of the European Union.
13. The device according to paragraph 10 to 12 connectable to a wired or wireless network.
14. The device according to paragraph 10 to 13 connectable to at least one further device.
15. The device according to paragraph 13 or 14 connectable to a hospital information system.
16. The device according to paragraph 10 to 15 comprising an output unit, such as a display and/or a printer, for providing the dosage recommendation.
17. The device according to paragraph 10 to 16 comprising a web server for providing input values and/or receiving drug dosage recommendations.
18. The device according to paragraph 10 to 17 comprising a data reader.
19. The device according to paragraph 10 to 18 comprising at least one sensor.
20. The device according to paragraph 19 comprising at least one haemoglobin sensor.
21. The device according to paragraph 20, wherein the device is integrated into, connectable or connected to an apparatus.
22. The device according to paragraph 21, wherein the apparatus is a haemodialysis machine, a hemofiltration or a hemodiafiltration machine.
23. A drug in a dosage recommended by the method and/or the device according to one of the preceding paragraphs.
24. The drug according to paragraph 23, wherein the drug is erythropoietin or an erythropoietin derivative such as Epoetin alfa, Epoetin beta, Darbepoetin alfa or Methoxy polyethylene glycol-epoetin beta.

The invention claimed is:

1. A computer-implemented method for recommending a dose of an erythropoiesis stimulating agent (ESA) and/or iron, the method performed using artificial intelligence and by an artificial neural network that has been trained using historical patient data, the method comprising:
   simulating effects to haemoglobin level of several different drug doses of the ESA and/or iron;
   determining a reward score for each drug dose of the several different drug doses, wherein the reward score is based on:
      a current haemoglobin level,
      a predicted haemoglobin level or a predicted change of haemoglobin level in response to the drug dose, and
      a target range of haemoglobin level; and
   selecting, based on a comparison of the reward scores of the several different drug doses, a recommended drug dose of the several different drug doses.

2. The method according to claim 1, wherein the artificial neural network is a multilayer perceptron feed-forward artificial neural network.

3. The method according to claim 1, wherein the historical patient data is dialysis patient data.

4. The method according to claim 1, wherein the training of the artificial neural network is adaptive.

5. A device configured to execute the method of claim 1.

6. A dose of the ESA and/or iron in the recommended drug dose selected using the method of claim 1.

7. A non-transitory computer-readable storage medium with an executable program stored thereon, wherein the program instructs a programmable computer system to execute the method of claim 1.

* * * * *

UNITED STATES PATENT AND TRADEMARK OFFICE
CERTIFICATE OF CORRECTION

| | |
|---|---|
| PATENT NO. | : 11,302,445 B2 |
| APPLICATION NO. | : 16/318753 |
| DATED | : April 12, 2022 |
| INVENTOR(S) | : Carlo Barbieri and Flavia Mari |

It is certified that error appears in the above-identified patent and that said Letters Patent is hereby corrected as shown below:

On the Title Page

OTHER PUBLICATIONS, Column 2, Line 5, delete "t itle" and insert --title--.

In the Specification

Column 1, Line 9, delete "EP 1617993.7, filed on Jul. 18, 2106," and insert --EP 16179993.7, filed on Jul. 18, 2016,--.

Signed and Sealed this
Twenty-sixth Day of July, 2022

Katherine Kelly Vidal
*Director of the United States Patent and Trademark Office*